(12) United States Patent
Akagane

(10) Patent No.: US 9,022,935 B2
(45) Date of Patent: May 5, 2015

(54) ULTRASOUND SURGERY SYSTEM

(71) Applicant: Olympus Medical Systems Corp., Tokyo (JP)

(72) Inventor: Tsunetaka Akagane, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/186,894

(22) Filed: Feb. 21, 2014

(65) Prior Publication Data

US 2014/0288465 A1    Sep. 25, 2014

Related U.S. Application Data

(63) Continuation of application No. PCT/JP2013/066225, filed on Jun. 12, 2013.

(60) Provisional application No. 61/695,885, filed on Aug. 31, 2012.

(51) Int. Cl.
*A61B 8/00* (2006.01)
*A61N 7/00* (2006.01)
(Continued)

(52) U.S. Cl.
CPC .......... *A61N 7/00* (2013.01); *A61B 17/320092* (2013.01); *A61B 2018/0072* (2013.01); *A61B 2018/00845* (2013.01); *A61B 2018/00988* (2013.01)

(58) Field of Classification Search
CPC ............. A61B 17/320068; A61B 2017/00017; A61B 2017/0003; A61B 2017/00973; A61M 1/0058; B06B 1/06; B06B 1/0607
USPC .................. 600/407, 437, 443, 441; 601/2
See application file for complete search history.

(56) References Cited

U.S. PATENT DOCUMENTS 5,823,962 A * 10/1998 Schaetzle et al. ............. 600/439
8,167,805 B2 * 5/2012 Emery et al. .................. 600/439
(Continued)

FOREIGN PATENT DOCUMENTS

EP    2 444 017 A1    4/2012
JP    A-7-303635    11/1995
(Continued)

OTHER PUBLICATIONS

International Search Report issued in International Search Report PCT/JP2013/066225 mailed Aug. 27, 2013.

*Primary Examiner* — Unsu Jung
*Assistant Examiner* — Joel Lamprecht
(74) *Attorney, Agent, or Firm* — Oliff PLC

(57) ABSTRACT

An ultrasound surgery system includes: a handpiece including an ultrasound transducer that generates ultrasound vibration and a treatment portion to which the ultrasound vibration is transmitted; a drive current output section provided in a power supply apparatus to which the handpiece is detachably connected, the drive current output section producing and outputting a drive current for driving the ultrasound transducer; a drive frequency output section that detects and outputs a drive frequency for driving the ultrasound transducer with a resonant frequency of the ultrasound transducer; a first information storage section that stores first information including a parameter unique to the handpiece; and a variable current setting section that variably sets the drive current produced by the drive current output section, based on the drive frequency detected by the drive frequency output section, in order to maintain an amplitude or a vibration velocity of the ultrasound vibration in the treatment portion at a predetermined value.

15 Claims, 10 Drawing Sheets

(51) Int. Cl.
*A61B 17/32* (2006.01)
*A61B 18/00* (2006.01)

(56) References Cited

U.S. PATENT DOCUMENTS

| | | | |
|---|---|---|---|
| 8,900,259 B2 * | 12/2014 | Houser et al. | ................ 606/169 |
| 2001/0039389 A1 | 11/2001 | Sakurai et al. | |
| 2007/0167881 A1 | 7/2007 | Takahashi | |
| 2010/0324580 A1 * | 12/2010 | Yamada | ................ 606/169 |

FOREIGN PATENT DOCUMENTS

| | | |
|---|---|---|
| JP | A-2001-258089 | 9/2001 |
| JP | A-2002-186901 | 7/2002 |
| JP | A-2006-43348 | 2/2006 |
| WO | WO 2010/146940 A1 | 12/2010 |

* cited by examiner

FIG.3

| ID | DRIVE CURRENT VALUE[A] | LOWER LIMIT VALUE[kHz] | UPPER LIMIT VALUE[kHz] | FREQUENCY RANGE[kHz] | INITIAL RESONANT FREQUENCY[kHz] |
|---|---|---|---|---|---|
| 0001 | 0.53 | 46.7 | 47.3 | 46.7–47.3 | 47.0 |
| 0002 | 0.54 | 46.9 | 47.5 | 46.9–47.5 | 47.2 |
| 0003 | 0.535 | 46.8 | 47.4 | 46.8–47.4 | 47.1 |
| ... | ... | ... | ... | ... | ... |

FIG.4

| ID | FIRST PARAMETER($\alpha$) | SECOND PARAMETER($\beta$) |
|---|---|---|
| 0001 | $\alpha 1$ | $\beta 1$ |
| 0002 | $\alpha 1$ | $\beta 1 - \Delta$ |
| 0003 | $\alpha 1$ | $\beta 1 + \Delta$ |
| 0004 | $\alpha 1 - \Delta$ | $\beta 1$ |
| ⋮ | ⋮ | ⋮ |
| 0011 | $\alpha 2$ | $\beta 2$ |
| 0012 | $\alpha 2$ | $\beta 2 - \Delta$ |
| 0013 | $\alpha 2$ | $\beta 2 + \Delta$ |
| 0014 | $\alpha 2 + \Delta$ | $\beta 2$ |
| ⋮ | ⋮ | ⋮ |

| ID | FIRST PARAMETER | SECOND PARAMETER |
|---|---|---|
| 0001 | $\alpha 1$ | $\beta 1$ |

| ID | DRIVE CURRENT VALUE[A] | INITIAL RESONANT FREQUENCY[kHz] |
|---|---|---|
| 0001 | 0.53 | 47.0 |

ULTRASOUND SURGERY SYSTEM

CROSS REFERENCE TO RELATED APPLICATION

This application is a continuation application of PCT/JP2013/066225 filed on Jun. 12, 2013 and claims benefit of U.S. Provisional Patent Application No. 61/695,885 filed in the U.S.A. on Aug. 31, 2012, the entire contents of which are incorporated herein by this reference.

BACKGROUND OF THE INVENTION

1. Field of the Invention

The present invention relates to an ultrasound surgery system for performing a surgery for therapy using ultrasound vibration.

2. Description of the Related Art

In recent years, ultrasound surgery systems for performing surgeries for treatment, such as dissection and/or coagulation, of a site of lesion utilizing ultrasound vibration, using a handpiece with an ultrasound transducer mounted therein have been used.

For example, Japanese Patent Laid-Open Publication No. 7-303635, which is a conventional art example, discloses a system that performs constant current control using phase-locked loop (PLL) control that drives an ultrasound transducer mounted in a handpiece while tracking a resonant frequency so as to, even if a load varies, drive the ultrasound transducer at the resonant frequency. Also, the related art example discloses a configuration in which switching of a characteristic of a low-pass filter is performed so as to perform stable PLL control.

Where an ultrasound transducer includes a langevin transducer that includes a plurality of annular ultrasound vibration elements fastened together via a bolt, some variation in characteristic occur among respective products.

SUMMARY OF THE INVENTION

An ultrasound surgery system according to an aspect of the present invention includes: a handpiece including an ultrasound transducer capable of generating ultrasound vibration and a probe joined to the ultrasound transducer, the probe being capable of transmitting the ultrasound vibration generated by the ultrasound transducer to a treatment portion; a power supply apparatus for driving the ultrasound transducer, the power supply apparatus allowing the handpiece to be connected thereto; a drive current output section provided in the power supply apparatus, the drive current output section being configured to produce a drive current for driving the ultrasound transducer and output the produced drive current to the ultrasound transducer; a drive frequency output section provided in the power supply apparatus, the drive frequency output section being configured to detect a drive frequency for driving the ultrasound transducer mounted in the handpiece, with a resonant frequency of the ultrasound transducer, and outputs the detected drive frequency; a first information storage section configured to store first information including a parameter based on identification information unique to the handpiece connected to the power supply apparatus, the first information being referred to when, in order to keep an amplitude or a vibration velocity of the ultrasound vibration in the treatment portion of the handpiece at a predetermined value according to the handpiece, a predetermined drive current value to be outputted to the ultrasound transducer, the predetermined drive current value corresponding to the predetermined value, is determined; and a variable current setting section provided in the power supply apparatus, the variable current setting section being configured to variably set the drive current so that the drive current produced by the drive current output section based on the parameter stored in the first information storage section and the drive frequency detected by the drive frequency output section has the predetermined drive current value, in order to keep the amplitude or the vibration velocity of the ultrasound vibration in the treatment portion provided at a distal end portion of the probe in the handpiece connected to the power supply apparatus at the predetermined value.

BRIEF DESCRIPTION OF THE DRAWINGS

FIG. 3 is a diagram illustrating an example of a look-up table stored in a flash memory;

FIG. 4 is a diagram illustrating an example of parameters stored in a parameter storage section;

DETAILED DESCRIPTION OF THE PREFERRED EMBODIMENT

An embodiment of the present invention will be described below with reference to the drawings.

First Embodiment

Figure 1:
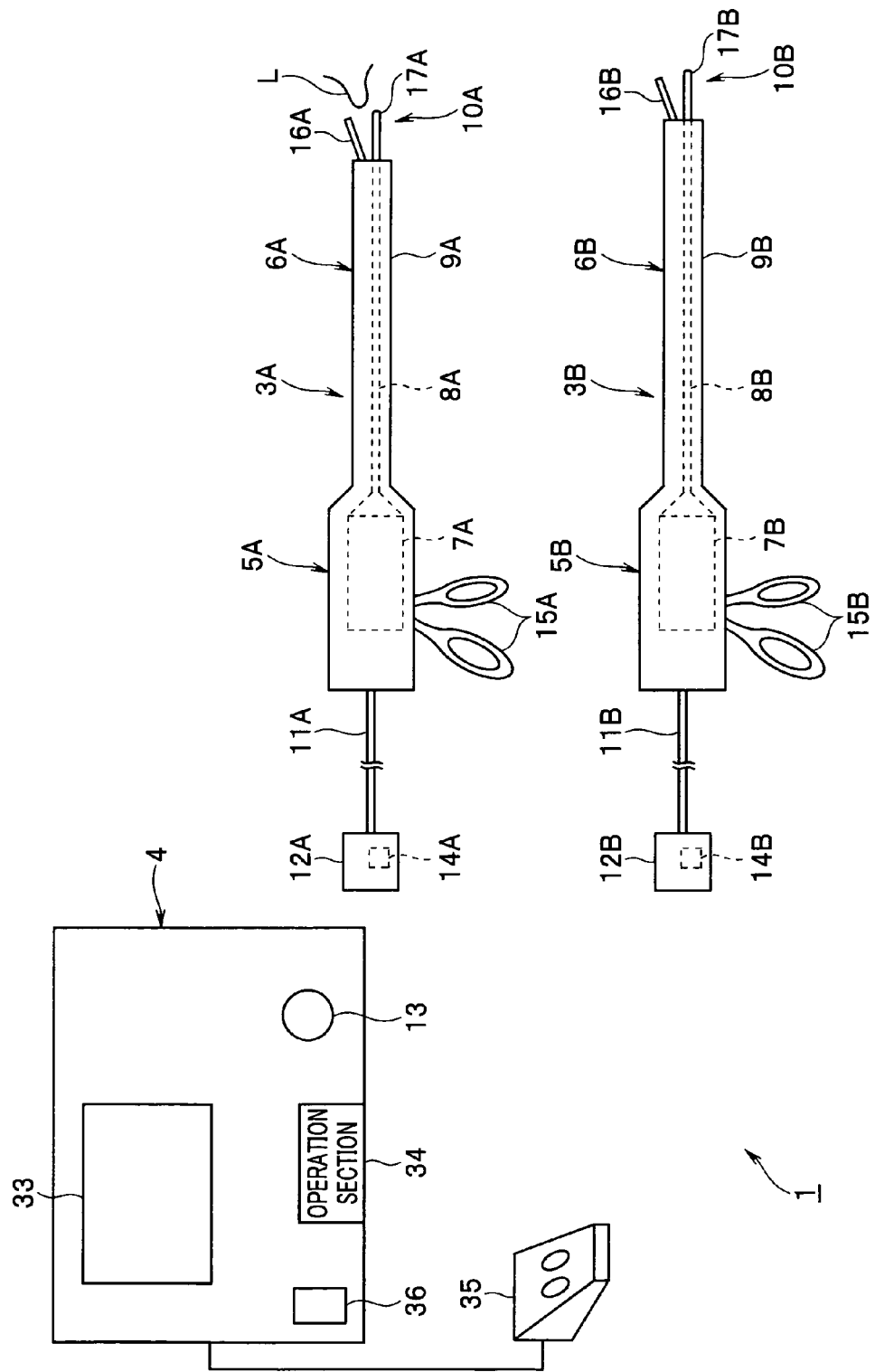
FIG. 1 is a diagram illustrating an overall configuration of an ultrasound surgery system according to a first embodiment of the present invention.

As illustrated in FIG. 1, an ultrasound surgery system 1 according to a first embodiment of the present invention includes different types of handpieces 3A and 3B for performing dissection and/or coagulation treatment of a living tissue L to be treated, and a power supply apparatus 4 to which either of the handpieces 3A and 3B is selectively detachably connected, the power supply apparatus 4 supplying drive power. Note that although FIG. 1 illustrates two types of handpieces 3A and 3B, any of handpieces 3J (J is A, B, . . . , N) of types that are the same as or different from the handpiece 3A or 3B can further be connected to the power supply apparatus 4.

Each handpiece 3J includes a grasping portion 5J to be grasped by a surgeon, and an elongated insertion portion (probe portion) 6J provided at a front end of the grasping portion 5J.

In each grasping portion 5J, an ultrasound transducer 7J that makes ultrasound vibration, and a proximal end of a probe stick (also referred to as "probe") 8J, which serves as an ultrasound transmission member that transmits the ultrasound vibration generated by the ultrasound transducer 7J, is joined to a front-side end face of the ultrasound transducer 7J.

The ultrasound transducer 7J includes a langevin transducer including a stack of a plurality of ultrasound vibration elements, each including an annular piezoelectric element P (see FIG. 2), fastened together via a bolt.

A distal end portion of each probe 8J inserted inside a sheath 9J forming a mantle tube of the respective insertion portion 6J projects from a distal end opening of the sheath 9J and forms a treatment portion 10J.

A surgeon brings the treatment portion 10J into contact with a living tissue L to be treated, enabling dissection and/or coagulation treatment of the living tissue L by means of the ultrasound vibration transmitted by the probe 8J.

Also, a signal cable 11J extends out from each grasping portion 5J, and a connector 12J provided at an end portion of the signal cable 11J is detachably connected to a connector receiver 13 in the power supply apparatus 4. Then, the ultrasound transducer 7J mounted in a handpiece 3J connected to the power supply apparatus 4 is driven by an AC drive current (output current) outputted from a later-described power amplifier 27 provided inside the power supply apparatus 4.

Note that even if the langevin transducers mounted in the respective handpieces 3J belong to a same type, there is some variation in characteristic among the respective products because each of the langevin transducers is manufactured by fastening a plurality of annular ultrasound vibration elements together via a bolt.

In the conventional example, a resonant frequency for each ultrasound transducer is detected and each ultrasound transducer is driven by a constant current (value) that is a reference current for the detected resonant frequency. However, because of variation among the respective products, there is a drawback (problem to be solved) that when each ultrasound transducer is driven by a constant current, an amplitude value or a vibration velocity value may be deviated from a predetermined amplitude value or a predetermined vibration velocity value that is suitable for treatment using ultrasound vibration.

As described above, since an amplitude or a vibration velocity of ultrasound vibration in each ultrasound transducer 7J is an important parameter that may impose a large effect on treatment performance when treatment such as dissection or coagulation of a living tissue L to be treated is performed, it is desired that a respective amplitude value or a respective vibration velocity value suitable for treatment can be set even if there is some variation in characteristic among the products.

In the present embodiment, attention is focused on a relationship between a drive frequency value, and an amplitude value or a vibration velocity value of ultrasound vibration when each ultrasound transducer is driven by a drive signal of a resonant frequency, and a drive current (output current) is variably controlled so that an amplitude value or a vibration velocity value suitable for treatment can be set even if there is a difference in characteristic (there is variation in characteristic), whereby the above problem is solved.

Each handpiece 3J includes a memory 14J that stores unique information or identification information (ID) for uniquely identifying the respective handpiece 3J. In the example illustrated in FIG. 1, the memory 14J is provided inside the connector 12J inside each handpiece 3J. Note that the present invention is not limited to the case where the memory 14J is provided in the connector 12J in each of the handpieces 3J, the memory 14J may be provided in a part other than the connector 12J. Also, e.g., a resistor having a resistance value corresponding to an ID or a bar code corresponding to an ID, rather than the memory 14J that stores ID information, may be used.

Each memory 14J provides a first information storage section that stores first information, which is at least referred to in order to maintain (or set) a predetermined value of amplitude or vibration velocity suitable for treatment when a drive current value corresponding to the predetermined value is acquired, where the treatment is performed using ultrasound vibration caused by the ultrasound transducer 7J mounted in the respective handpiece 3J. The ID stored in the memory 14J provides the first information, which is referred to when the drive current value is acquired. Note that if the first information is provided as an ID, the ID alone is insufficient to determine the predetermined drive current value, and thus, information other than the ID is further referred to for acquisition of the predetermined drive current value.

Also, the predetermined value of amplitude or vibration velocity suitable for treatment is actually a value set for a position of the treatment portion 10J provided at the distal end portion of the probe 8J to which ultrasound vibration of the ultrasound transducer 7J is transmitted via the probe 8J. This is because the treatment portion 10J is brought into contact with a living tissue L to be treated such as a diseased site and treatment for therapy is performed using the ultrasound vibration at the position of the treatment portion 10J. Ordinarily, the treatment portion 10J is used in such a manner that the treatment portion 10J is integrally joined to the ultrasound transducer 7J via the probe 8J, and thus, in the present description, a description of the ultrasound transducers that generate a predetermined value of amplitude or vibration velocity suitable for treatment is also provided with no reference to the treatment portions 10J.

Also, although a first predetermined value of amplitude suitable for treatment or a second predetermined value of vibration velocity suitable for treatment is simply expressed as a predetermined value of amplitude or vibration velocity suitable for treatment, to be exact, the first predetermined value for amplitude and the second predetermined value for vibration velocity are different from each other in terms of value and unit.

In each grasping portion 5J, finger rest portions 15J, which are opened/closed by a surgeon with his fingers rested thereon, are provided. As a result of an operation to open/close the finger rest portions 15J, a movable piece 16J, which forms one of parts of the treatment portion 10J, is pivoted with reference to a proximal end thereof. Consequently, the living tissue L to be treated is grasped between a probe distal end portion 17J, which forms the other of the parts of the treatment portion 10J and the movable piece 16J to perform treatment. Note that treatment of the living tissue L to be treated may be performed using the probe distal end portion 17J alone, without provision of the finger rest portions 15J and the movable piece 16J.

Figure 2:
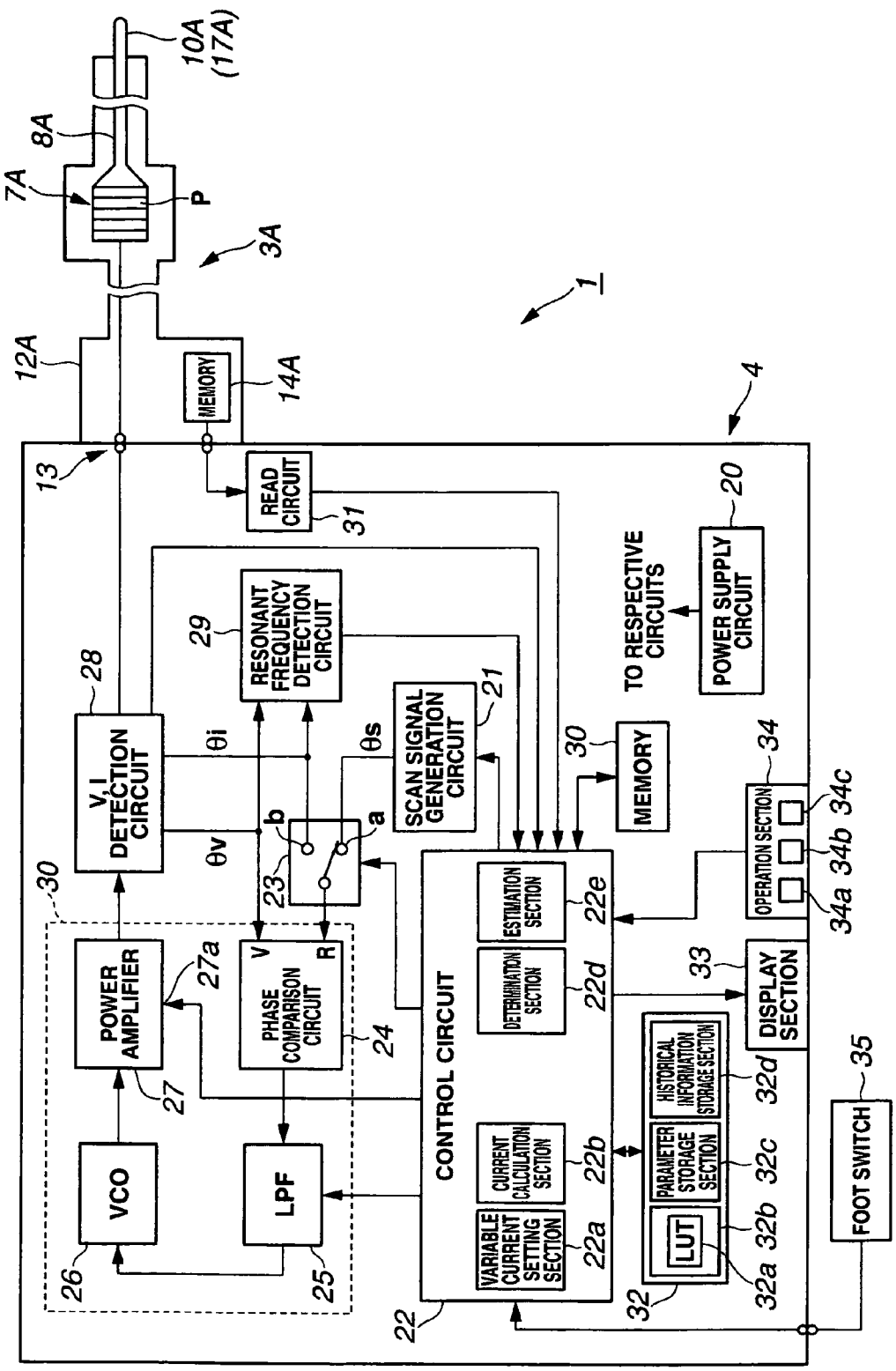
FIG. 2 is a block diagram illustrating an inner configuration of a power supply apparatus included in the ultrasound surgery system.

As illustrated in FIG. 2, the power supply apparatus 4 includes a power supply circuit 20 that produces DC power from a commercial power supply. The power supply circuit 20 supplies respective circuits inside the power supply apparatus 4 with DC power necessary for operation.

The power supply apparatus 4 includes a scan signal generation circuit 21 that generates a scan signal θs whose frequency (also referred to as "drive frequency") varies to produce a drive signal (before current amplification), in order to make the ultrasound transducer 7J and the probe 8J of a handpiece 3J connected to the power supply apparatus 4 have ultrasound vibration with a resonant frequency therefor.

The scan signal generation circuit 21 generates a scan signal θs that scans (or sweeps) a predetermined range of frequencies so that the scan signal θs including a resonant frequency can be applied to the ultrasound transducer 7J and the probe 8J mounted in any handpiece 3J from among a single type or plural types of handpiece 3J to be connected to the power supply apparatus 4.

In the present embodiment, the scan signal generation circuit 21 generates a scan signal θs that covers, for example, around 46.0 to 48.0 kHz as a predetermined range of frequencies with 47 kHz as a central frequency, the a predetermined range including frequencies around the central frequency. However, the present invention is not limited to the case where the scan signal θs is generated within such range. For example, a scan signal generation circuit that scans a wider range of frequencies or one that generates a scan signal θs in a frequency range with a central frequency that is different from 47 kHz when scanning is performed according to resonant frequency characteristics of the ultrasound transducer 7J and the probe 8J may be employed. Also, one may be employed that generates a scan signal θs in a wider frequency range so as to respond to a case where different types of ultrasound transducers 7J and probes 8J are provided.

The scan signal generation circuit 21 may be provided using a voltage-controlled oscillation circuit (abbreviated as "VCO circuit") that outputs scan signals θs with different oscillation frequencies according to, for example, values of applied input voltages.

The scan signal generation circuit 21 outputs a scan signal θs whose oscillation frequency substantially successively varies according to a predetermined range of voltage signal for control, which is outputted from a control circuit 22.

The (voltage signal of the) scan signal θs is applied to one of input ends, more specifically, a reference-side input end R of a phase comparison circuit 24 that performs phase comparison, via a contact a in a switch circuit 23, switching of which is controlled by the control circuit 22.

A voltage phase signal θv from a voltage and current detection circuit (abbreviated as "V, I detection circuit" in FIG. 2) 28 that detects a voltage and a current is applied via a power amplifier 27 to the other input end, more specifically, a variable-side input end V of the phase comparison circuit 24.

The phase comparison circuit 24 compares phases of the two signals inputted from the two input ends to perform conversion to a voltage signal corresponding to a phase difference from the scan signal θs applied to the reference-side input end R and outputs the voltage signal. The voltage signal is inputted to a low-pass filter (abbreviated as "LPF") 25 that extracts a DC component, and the LPF 25 outputs a control voltage close to direct current to a VCO circuit 26.

Note that if switching is made so as to turn on a contact b in the switch circuit 23, a current phase signal θi from the voltage and current detection circuit 28 is applied to the reference-side input end R.

The VCO circuit 26 outputs an oscillation signal of a frequency according to the control voltage close to direct current to the power amplifier 27 that performs current amplification. The power amplifier 27 performs current amplification to produce and output a drive current, which serves as a drive signal with a current value for driving an ultrasound transducer 7J with a sufficient amplitude or vibration velocity secured.

In other words, the power amplifier 27 provides a drive current output section (or a drive signal output section) that produces a drive current (drive signal) for driving an ultrasound transducer 7J and outputs the produced drive current to the ultrasound transducer 7J.

The power amplifier 27 is formed by a current amplification factor-varying amplifier whose current amplification factor varies according to a voltage value applied to a current amplification factor control end 27a. The control circuit 22 variably controls (variably sets) a value of a drive current (output current) that drives the ultrasound transducer 7J, which is outputted from the power amplifier 27, by varying a value of control voltage applied to the current amplification factor control end 27a. Thus, the control circuit 22 has a function of a variable current setting section 22a that variably sets (variably controls) a drive current produced or outputted by the power amplifier 27, which provides a drive current output section.

The drive signal outputted from the power amplifier 27 is inputted to the voltage and current detection circuit 28 that detects the voltage phase signal θv and the current phase signal θi for the drive signal.

The drive signal outputted from the power amplifier 27 is applied via the voltage and current detection circuit 28 to the ultrasound transducer 7J mounted in the handpiece 3J connected to the connector receiver 13.

The voltage and current detection circuit 28 outputs the voltage phase signal θv and the current phase signal θi for the drive signal outputted from the power amplifier 27 when the ultrasound transducer 7J is driven, to a resonant frequency detection circuit 29 that detects a resonant frequency. Also, the voltage and current detection circuit 28 outputs the voltage phase signal θv to the phase comparison circuit 24, and outputs the current phase signal θi to the phase comparison circuit 24 via the contact b in the switch circuit 23. Here, the voltage phase signal θv is a voltage detection signal indicating variation of a voltage of an ultrasound drive signal applied to opposite ends of the ultrasound transducer 7J (in other words, variation in phase of the voltage), and the current phase signal θi is a current detection signal indicating variation of a current flowing in the ultrasound transducer 7J (in other words, variation in phase of the current varies).

The phase comparison circuit 24, the LPF 25, the VCO 26 and the power amplifier 27 provides a PLL circuit 30 that performs PLL control. Note that it is also possible to define the PLL circuit 30 as being formed by a circuit including the switch circuit 23.

Note that if the scan signal generation circuit 21 outputs a scan signal θs whose frequency varies, the drive signal outputted from the power amplifier 27 becomes a drive signal with a frequency that varies so as to follow the scan signal θs whose frequency varies and with current amplified even where the PLL circuit 30 is provided. Also, if the scan signal θs whose frequency varies is outputted for resonant frequency detection, filter characteristics of the LPF 25 may be changed.

More specifically, a pass band of the LPF 25 may be widened to set characteristics that makes it easy to follow (track) frequency variation (which can also be referred to as phase variation), and the pass band of the LPF 25 may be narrowed after the resonant frequency detection.

The resonant frequency detection circuit 29 detects the voltage phase signal θv and the current phase signal θi when the scan signal θs whose frequency has been varied is outputted from the scan signal generation circuit 21, and determines whether or not a resonant frequency state (of the ultrasound transducer 7J and the probe 8J) in which the voltage phase signal θv and the current phase signal θi correspond to each other in phase is achieved.

The resonant frequency detection circuit 29 is provided by a phase difference detection circuit in which a difference in phase between two phase signals becomes minimum. Since an impedance where the ultrasound transducer 7J is a load becomes minimum at a resonant frequency, the resonant frequency detection circuit 29 may be formed using an impedance detection circuit (or a minimum impedance value detection circuit) that detects a frequency at which the impedance of the ultrasound transducer 7J becomes minimum, as a resonant frequency from the voltage phase signal θv and the current phase signal θi.

Upon detection of a resonant frequency, the resonant frequency detection circuit 29 outputs a detection signal for the resonant frequency to the control circuit 22. Upon input of the detection signal, the control circuit 22 immediately switches the switch circuit 23 so as to cause the current phase signal θi in the resonant frequency state to be inputted to the reference-side input end R of the phase comparison circuit 24.

After the switching of the switch circuit 23 as described above, a drive frequency of the drive signal outputted from the power amplifier 27 is controlled so as to follow the resonant frequency in a state in which a PLL control loop is formed.

For more detailed description, the current phase signal θi for the drive signal with the resonant frequency is inputted to the reference-side input end R of the phase comparison circuit 24 as a reference signal, and the voltage phase signal θv for the drive signal is inputted to the variable-side input end V. The phase comparison circuit 24 outputs a voltage signal corresponding to a phase difference between the current phase signal θi and the voltage phase signal θv to the LPF 25. The VCO circuit 26, to which the control voltage changed to a DC voltage through the LPF 25 is applied, outputs an oscillation signal that depends on a value of the control voltage outputted from the LPF 25, to the power amplifier 27. The power amplifier 27 drives the ultrasound transducer 7J via the drive signal with current amplified. The power amplifier 27 drives the ultrasound transducer 7J and also feeds the voltage phase signal θv back to the variable-side input end V of the phase comparison circuit 24 via the voltage and current detection circuit 28, and applies the current phase signal θi to the reference-side input end R of the phase comparison circuit 24. Consequently, a PLL control loop is formed.

The PLL control loop provides a control state in which the drive signal outputted from power amplifier 27 tracks the drive frequency corresponding to the resonant frequency of the ultrasound transducer 7J.

Also, the voltage and current detection circuit 28 outputs (effective values or peak values) of a voltage value V and a current value I when the ultrasound transducer 7J is driven by the drive signal with the resonant frequency, to the control circuit 22.

In the present embodiment, the control circuit 22 performs control so that when the ultrasound transducer 7J is driven by the drive signal with the resonant frequency, in order to provide a predetermined value of amplitude or vibration velocity suitable for treatment, a value of the drive current outputted from the power amplifier 27 to the ultrasound transducer 7J becomes a predetermined drive current value corresponding to the predetermined value.

Note that it is also possible that when the resonant frequency detection circuit 29 detects a resonant frequency, the resonant frequency detection circuit 29 performs control to switch the switch circuit 23 to form a PLL control loop, not via the control circuit 22.

The present embodiment is configured so that when the resonant frequency detection circuit 29 detects a resonant frequency, the resonant frequency can be recognized by the control circuit 22.

More specifically, if the scan signal generation circuit 21 is provided by a VCO circuit, based on (a voltage value of) a voltage signal for control, which is outputted from the control circuit 22 to the VCO circuit at the timing of detection of a resonant frequency, the control circuit 22 can recognize (or calculate) the relevant resonant frequency. Alternatively, it is possible that when the resonant frequency detection circuit 29 detects a resonant frequency, a detection signal is sent to the scan signal generation circuit 21 as well as the control circuit 22, and an oscillation frequency of a scan signal θs outputted by the scan signal generation circuit 21 is outputted to the control circuit 22. Then, the control circuit 22 stores information on the detected resonant frequency in, for example, a memory 30. The memory 30 provides a resonant frequency information storage section that stores information on a detected resonant frequency.

When a drive signal for treatment is outputted from the power amplifier 27 in a PLL control loop state resulting from switching of the switch circuit 23, the control circuit 22 determines a resonant frequency detected by the resonant frequency detection circuit 29, as a drive frequency. Then, the control circuit 22 performs control of the current amplification factor of the power amplifier 27 so as to provide a drive current value suitable for the treatment at the drive frequency.

The power supply apparatus 4 further includes a read circuit 31 that reads an ID in the memory 14J in a handpiece 3J connected to the power supply apparatus 4, and a flash memory 32, which serves as an information storage section that stores first information that is referred to for acquisition of a predetermined drive current value corresponding to a predetermined value of amplitude or vibration velocity of ultrasound vibration of ultrasound transducer 7J, which is suitable for treatment, or second information for calculation of the predetermined drive current value.

Upon a handpiece 3J being connected to the power supply apparatus 4, the read circuit 31 reads the ID of the connected handpiece 3J from the memory 14J, and outputs the read ID to the control circuit 22.

The flash memory 32 includes an LUT storage section 32b that stores a predetermined drive current value associated with an ID as first information for acquisition of a predetermined drive current value corresponding to the predetermined value of amplitude or vibration velocity, in the form of a look-up table (abbreviated as LUT) 32a. FIG. 3 indicates an example of an LUT 32a. As illustrated in FIG. 3, IDs are stored in such a manner that each ID is associated with a predetermined drive current value (abbreviated simply as "drive current value" in FIG. 3) suitable for treatment in the respective handpiece 3J. The control circuit 22 acquires a corresponding predetermined drive current value from the ID, and controls the current amplification factor of the power amplifier 27 so as to provide the acquired predetermined drive current value.

Then, the control circuit 22 locks the control voltage value so as to lock the current amplification factor of the power amplifier 27 when a current detected by the voltage and current detection circuit 28 reaches the predetermined drive current value. Also, the control circuit 22 may store the control voltage value in this case in, for example, the memory 30.

Accordingly, after the locking of the current amplification factor of the power amplifier 27, the ultrasound transducer 7J is driven by a drive signal tracking the resonant frequency, which is outputted from the drive signal output section (or the drive current output section) included in a PLL control loop. Also, the ultrasound transducer 7J maintains an ultrasound vibration state in which ultrasound vibration of the treatment portion 10J at the distal end portion of the probe 8J keeps a predetermined value of amplitude or vibration velocity suitable for treatment.

Note that the memory 30, which stores the control voltage value for setting the current amplification factor of the power amplifier 27 to a predetermined drive current value provides an information storage section or an information storage device that stores information for setting a drive current outputted from the power amplifier 27 (which provides a drive current output section or a drive current output circuit) to a predetermined drive current value suitable for treatment.

In the present embodiment, for each handpiece 3J, which is connected to the power supply apparatus 4 for use, a predetermined drive current value corresponding to a predetermined value of amplitude or vibration velocity of the ultrasound transducer 7J (and the probe 8J including the treatment portion 10J) mounted in the handpiece 3J, which is suitable for treatment, is found out in advance before the handpiece 3J is shipped as a product, and the predetermined drive current values associated with the respective IDs are stored as in the LUT 32a in FIG. 3.

The control circuit 22 refers to an ID read by the read circuit 31 to acquire a predetermined drive current value corresponding to the ID from the LUT 32a, and controls the current amplification factor of the power amplifier 27 so as to provide the acquired predetermined drive current value.

Thus, the control circuit 22 has a function of the variable current setting section 22a or a variable current setting apparatus that, in order to keep an amplitude or a vibration velocity of ultrasound vibration of the treatment portion 10J provided at the distal end portion of the probe 8J of a handpiece 3J detachably and selectively connected to the power supply apparatus 4, at a predetermined value (suitable for treatment), variably sets a drive current produced by the power amplifier 27, which serves as a drive current output section, based on a drive frequency detected by the drive frequency output section.

Also, as described above, the variable current setting section 22a acquires a predetermined drive current value corresponding to an ID from the LUT 32a in the LUT storage section 32b to variably set a drive current produced by the drive current output section to a predetermined drive current value corresponding to the predetermined value.

Also, as described below, the control circuit 22 may be configured to have a function of a current calculation section 22b. Based on the predetermined drive current value calculated by the current calculation section 22b, the variable current setting section 22a variably sets the drive current produced by the drive current output section to a predetermined drive current value corresponding to the predetermined value.

As described above, in the present embodiment, it is possible to, even if a resonant frequency for the ultrasound transducer 7J and the probe 8J joined to the ultrasound transducer 7J mounted in a handpiece 3J connected to the power supply apparatus 4 varies depending to the product, set a drive frequency to the resonant frequency and set a predetermined drive current value corresponding to a predetermined value of amplitude or vibration velocity suitable for treatment to drive the ultrasound transducer 7J.

The power supply apparatus 4 further includes a display section 33 that displays information on, e.g., a drive current value of a drive current outputted by the power amplifier 27, and an operation section 34 for performing various types of setting operations, the operation section 34 including a scan start button 34a for an operation to start generation of a scan signal θs whose frequency varies by the scan signal generation circuit 21 to detect a resonant frequency for the ultrasound transducer 7J. Also, a foot switch 35 for turning on/off an output of a drive signal is connected to the power supply apparatus 4. Also, as illustrated in FIG. 1, the power supply apparatus 4 includes a power supply switch 36 for power on/off.

Note that a scan signal θs may be generated via an output button rather than the scan start button 34a. Also, the scan start button 34a or the output button may be provided in a part other than the operation section 34.

Also, although the control circuit 22 may perform control so as to detect a resonant frequency after generation of a scan signal θs via the scan start button 34a or continuously drive the ultrasound transducer 7J after setting of a predetermined drive current value, preliminary settings for an output start may be made. In this case, upon completion of preliminary processing for resonant frequency detection and predetermined drive current value setting, in response to an operation to turn on an output via the foot switch 35, the control circuit 22 forms a PLL control loop at a resonant frequency, using the resonant frequency stored in the memory 30 and a control voltage value for setting to the predetermined drive current value, and drives the ultrasound transducer 7J at the predetermined drive current value from the power amplifier 27 based on the control voltage value.

Also, in the power supply apparatus 4 according to the present embodiment, the control circuit 22 can perform control (make settings) to acquire, from an ID, a corresponding predetermined drive current value and drive the ultrasound transducer 7J with the acquired predetermined drive current value, and also can perform control to calculate a predetermined drive current value suitable for treatment with reference to information on parameters associated with the ID and drive the ultrasound transducer 7J with the calculated predetermined drive current value.

Thus, for example, the flash memory 32 includes a parameter storage section 32c that stores data on parameters for calculating a predetermined drive current value for an ID, from the ID, as well as the LUT storage section 32b. Note that the parameter storage section 32c may be stored in a memory, a storage device or the like that is different from the flash memory 32. FIG. 4 illustrates an example of parameters stored in the parameter storage section 32c. Note that in FIG. 4, Δ indicates a value that is small compared to a value such as α1 and β1.

Figure 5A:
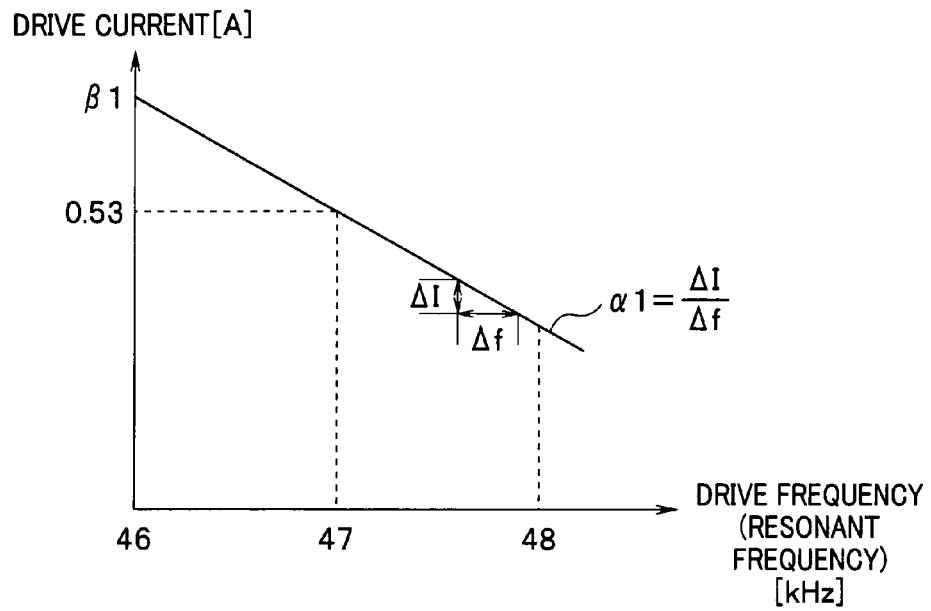
FIG. 5A is a characteristic diagram illustrating a relationship between drive frequency and drive current for an ultrasound transducer mounted in a handpiece.
Figure 5B:
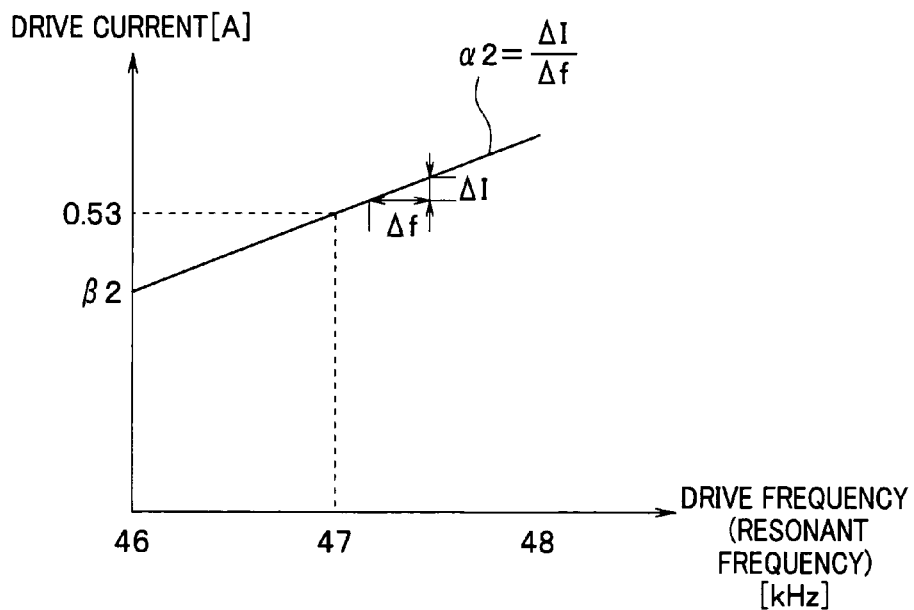
FIG. 5B is a characteristic diagram illustrating a relationship between drive frequency and drive current for an ultrasound transducer mounted in a handpiece of a type that is different from that in FIG. 5A.

Also FIGS. 5A and 5B each illustrate an example of characteristics for calculating a predetermined drive current value using parameters.

As illustrated in FIG. 5A or 5B, a first parameter α and a second parameter β indicated in FIG. 4 is parameters for determining a drive frequency (or resonant frequency)-drive current (predetermined drive current value) characteristic that varies according to characteristics such as a size or a material of the ultrasound transducer 7J (for example, a langevin transducer) mounted in a handpiece 3J and/or characteristics such as (a Young's modulus of) a material, a length or a thickness of the probe 8J, and indicates a drive current that makes a distal end amplitude of the probe 8J constant through different drive frequencies. Note that as can be seen from FIG. 5A or 5B, the first parameter α is calculated by a drive current variation amount ΔI relative to a small frequency variation amount Δf, that is, α=ΔI/Δf, and the second parameter β is a drive current value when a drive frequency f is a predetermined value (46 kHz in the illustrated example).

For example, in the ultrasound transducer 7A mounted in the handpiece 3A illustrated in FIG. 1, it has been found out that a relationship between a resonant frequency when the probe 8A is integrated and a predetermined drive current value (simply indicated as drive current in the Figure) suitable for treatment varies as in FIG. 5A. FIG. 5A indicates an example in which the probe distal end amplitude can be made constant by making settings so that where the drive frequency is a variable, as the drive frequency is larger, the drive current is smaller.

On the other hand, in the ultrasound transducer 7B mounted in the handpiece 3B illustrated in FIG. 1, which is of a type that is different from the handpiece 3A, a relationship between a drive frequency for driving at a resonant frequency when the probe 8B is integrated and a predetermined drive current value (drive current) suitable for treatment varies as in FIG. 5B. FIG. 5B indicates an example in which the probe distal end amplitude can be made constant by making settings so that as the drive frequency is larger, the drive current is larger.

In the cases of FIGS. 5A and 5B, it has been found out that that a drive current I(f)[A] can be approximated with good accuracy by a linear function using first and second parameters α and β for drive frequencies f[kHz] within a range of frequencies around a central frequency 47 kHz, which includes the central frequency 47 kHz:

$$I(f)=\alpha(f-46)+\beta \qquad (1).$$

Thus, the parameter storage section 32c in the present embodiment finds out values of first and second parameters α and β, which can be calculated by equation (1), in advance together with drive frequencies f, and associates the first and second parameters α and β with IDs and stores the first and second parameters α and β as illustrated in FIG. 4. For example, in the case of a handpiece with an ID of 0001, if a resonant frequency detected by the resonant frequency detection circuit 29 is assigned to equation (1) using a drive frequency f1 and parameters α1 and β1, a corresponding drive current I(f1) is calculated as a drive current value.

As described above, where parameters α and β are used, the control circuit 22 may have a function of the current calculation section 22b for calculating a predetermined drive current value suitable for treatment using an ID and parameters α and β in the parameter storage section 32c. More specifically, the current calculation section 22b has a function of a current calculation section that depends on a linear function such as indicated by equation (1). Also, the current calculation section 22b has a function of a current calculation section with a characteristic (α1<0) such as indicated in FIG. 5A and a characteristic (α2>0) such as indicated in FIG. 5B. Note that the current calculation section 22b may include a storage section that stores parameters α and β to be used for calculation.

Although a drive current suitable for treatment can more easily be calculated using the LUT 32a indicated in FIG. 3, rather than using the parameters α and β indicated in FIG. 4, use of the parameters α and β indicated in FIG. 4 provides the advantage of making it easy to collectively manage handpieces with similar characteristics.

In other words, in the case of handpieces with similar characteristics, the handpieces are similar to each other in terms of values of the first parameter α and the second parameter β, and thus, when a handpiece is repeatedly used, conditions for determining whether or not the handpiece can further be used can easily be set. For more specific description, in the case of those with similar characteristics, a research is made of, e.g., characteristic change and/or lifetime when each of an arbitrary number of sample handpieces is repeatedly used, whereby indications such as characteristic change and/or lifetime of the whole handpieces with similar characteristics can be obtained. In the present embodiment, for example, a case where a user such as a surgeon acquires a predetermined drive current value using the LUT storage section 32b or a case where a predetermined drive current value is calculated by the current calculation section 22b using the parameters α and β can be selected by a selection operation via a selection button 34c provided in the operation section 34.

Note that where a handpiece 3J (or an ultrasound transducer 7J) is repeatedly used, ultrasound vibration characteristics thereof vary because of, e.g., temporal change, and thus, it is desirable to determine whether or not the characteristics allows maintenance of a predetermined value that enables easy treatment. Thus, in the present embodiment, it is possible that: if a characteristic of a resonant frequency detected by the resonant frequency detection circuit 29 varies because of, e.g., temporal change, a lower limit value and an upper limit value of a range of variation of a resonant frequency that allows maintenance of a characteristic enabling easy treatment is found out in advance; and as illustrated in FIG. 3, an acceptable frequency range determined by the lower limit value and the upper limit value may be stored. Note that as illustrated in FIG. 3, data on a resonant frequency measured in advance in an initial state is stored in the LUT 32a.

Then, when the handpiece 3J is connected to the power supply apparatus 4 for use, the control circuit 22 determines whether or not the handpiece 3J is suitable for use by determining whether or not a resonant frequency detected by the resonant frequency detection circuit 29 is within the aforementioned frequency range. In other words, as illustrated in FIG. 2, the control circuit 22 may have a function of a determination section 22d that determines whether or not a handpiece 3J connected to the power supply apparatus 4 is suitable for use.

Although in the present embodiment, when a predetermined drive current value is determined, either or both of the LUT storage section 32b and the current calculation section 22b can be used, only either one of the LUT storage section 32b and the parameter storage section 32c may be provided to acquire or calculate a predetermined drive current value using the one alone.

Also, in the present embodiment, information on use history of a handpiece 3J used in connection with the power supply apparatus 4 is stored in the flash memory 32. Thus, the flash memory 32 has a function of a historical information storage section 32d that stores historical information.

Also, the control circuit 22 may have a function of an estimation section 22e that estimates (or evaluates) a period of time during which characteristics that allow easy treatment can be maintained for a repeatedly-used handpiece 3J, using the historical information stored in the historical information storage section 32d.

The variable current setting section 22a, the current calculation section 22b, the determination section 22d and the estimation section 22e provided by the control circuit 22 illustrated in FIG. 2 as described above may be provided by, e.g., a dedicated variable current setting circuit, a dedicated current calculation circuit, a dedicated current determination circuit, a dedicated comparison circuit and a dedicated estimation circuit, respectively.

Also, each of the LUT storage section 32b, the parameter storage section 32c and the historical information storage section 32d may be provided by, e.g., a separate storage device or a separate semiconductor memory.

The ultrasound surgery system 1 according to the present embodiment configured described above includes: a handpiece 3J including an ultrasound transducer 7J capable of generating ultrasound vibration and a probe 8J joined to the ultrasound transducer 7J, the probe 8J being capable of transmitting the ultrasound vibration generated by the ultrasound transducer 7J to a treatment portion 10J; a power supply apparatus 4 for driving the ultrasound transducer 7J, the power supply apparatus 4 allowing the handpiece 3J to be connected thereto; the power amplifier 27 provided in the power supply apparatus 4, the power amplifier 27 serving as a drive current output section that produces a drive current for driving the ultrasound transducer 7J and outputs the produced drive current to the ultrasound transducer 7J; the resonant frequency detection circuit 29 provided in the power supply apparatus 4, the resonant frequency detection circuit 29 serving as a drive frequency output section that detects a drive frequency for driving the ultrasound transducer 7J mounted in the handpiece 3J with a resonant frequency therefor and outputs the detected drive frequency; and the variable current setting section 22a provided in the power supply apparatus 4, the variable current setting section 22a, in order to keep an amplitude or a vibration velocity of the ultrasound vibration in the treatment portion 10J provided at a distal end portion of the probe 8J at a predetermined value, variably setting the drive current produced by the drive current output section based on the drive frequency detected by the drive frequency output section. Note that if the ultrasound transducer 7J, the treatment portion 10J, the probe 8J, . . . , and the variable current setting section 22a that have been defined above are components essential to the ultrasound surgery system 1 according to the present embodiment, components other than the essential components may be selectively removed or provided as necessary.

Figure 6:
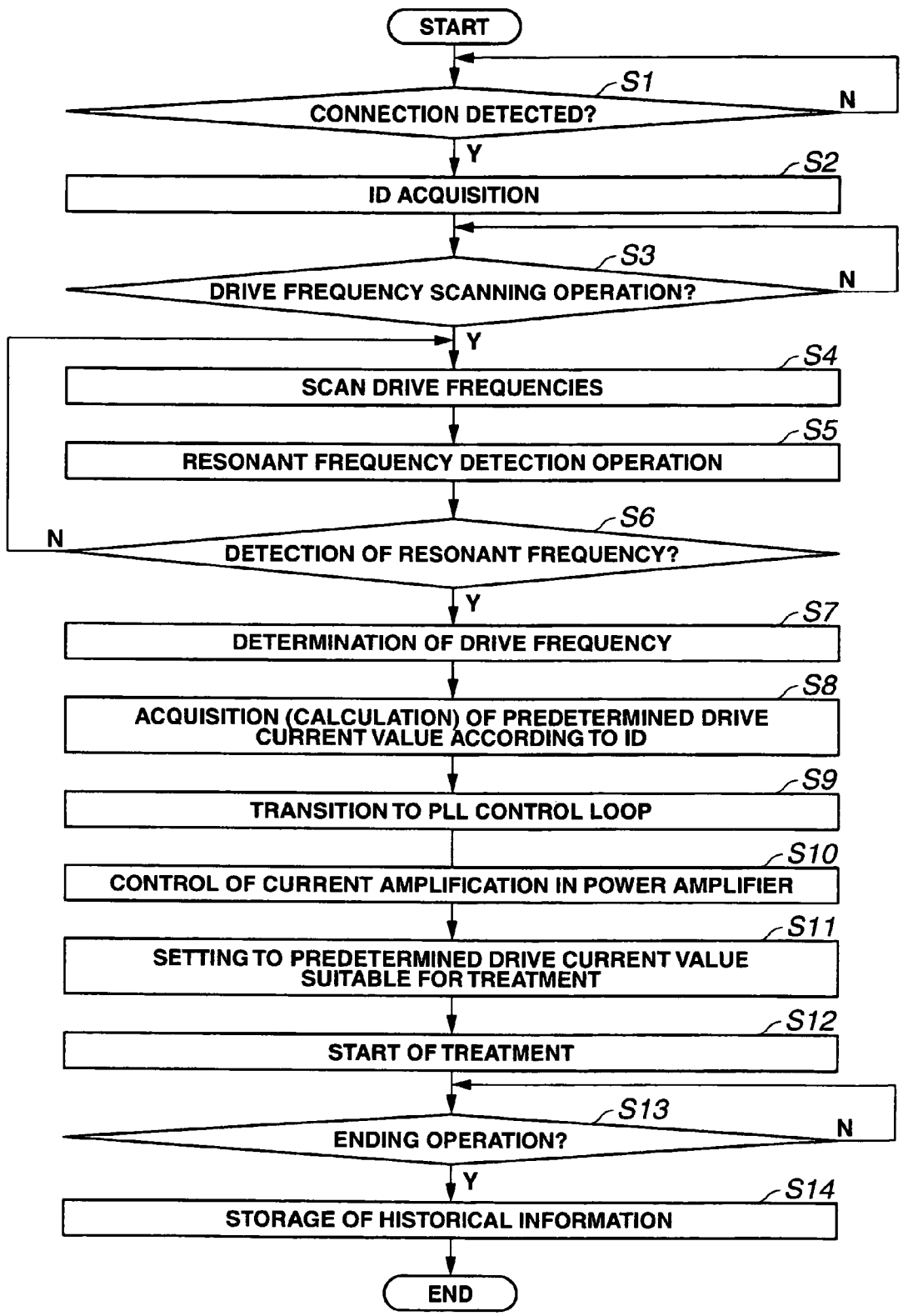
FIG. 6 is a flowchart illustrating, e.g., a processing procedure in the ultrasound surgery system according to the first embodiment.

Next, an operation of the present embodiment will be described with reference to FIG. 6. FIG. 6 indicates a content of basic processing in the ultrasound surgery system 1 according to the present embodiment.

A surgeon connects a handpiece (the handpiece is denoted as 3A) to be used for actually performing treatment to the power supply apparatus 4, and turns the power supply switch 36 on.

Then, in first step S1, the control circuit 22 determines (detects) whether or not the handpiece 3A is connected to the power supply apparatus 4, by determining whether or not the ID stored in the memory 14A of the handpiece 3A can be read. Thus, the control circuit 22 performs control so that the read circuit 31 reads the ID, and if the read circuit 31 reads the ID from the memory 14A and outputs the ID to the control circuit 22, the control circuit 22 determines that the handpiece 3A is connected to the power supply apparatus 4.

Also, if the connection is detected, in other words, the read circuit 31 reads the ID, as illustrated in step S2, the control circuit 22 acquires the ID and temporarily stores the ID in, e.g., the memory 30.

In next step S3, the control circuit 22 determines whether or not an operation to scan drive frequencies is performed, to wait for such operation to be performed.

If the operation to scan drive frequencies is performed, in next step S4, the control circuit 22 sends a control signal to the scan signal generation circuit 21 to perform control so that the scan signal generation circuit 21 generates a scan signal θs. In this case, the control circuit 22 performs switching control so that the contact a in the switch circuit 23 is connected to the scan signal generation circuit 21.

Then, the scan signal generation circuit 21 generates a scan signal θs. In other words, the scan signal generation circuit 21 generates a scan signal θs whose drive frequency varies.

Also, as indicated in step S5, in conjunction with the operation of the scan signal generation circuit 21 to generate the scan signal θs, the resonant frequency detection circuit 29 performs an operation to detect (determine) whether or not the drive frequency reaches a resonant frequency for the ultrasound transducer 7A.

In next step S6, the control circuit 22 monitors a detection signal from the resonant frequency detection circuit 29 to determine whether or not the drive frequency corresponds to the resonant frequency (the resonant frequency is detected). If the drive frequency does not correspond to the resonant frequency, the control circuit 22 performs control so as to continue the operations of the scan signal generation circuit 21 and the resonant frequency detection circuit 29. In other words, the scan signal generation circuit 21 continues the operation to generate the scan signal θs whose drive frequency varies, which is indicated in step S4. Also, the resonant frequency detection circuit 29 continues the operation to detect the resonant frequency, which is indicated in step S5.

As a result of repetition of processing in steps S4 to S6 in FIG. 6, the scan signal θs generated by the scan signal generation circuit 21 reaches the drive frequency corresponding to the resonant frequency. If the scan signal θs reaches the drive frequency corresponding to the resonant frequency, as indicated in step S7, the resonant frequency detection circuit 29 outputs a detection signal indicating the detection of the resonant frequency to the control circuit 22, and the control circuit 22 determines that the detected resonant frequency is used as a drive frequency for driving the ultrasound transducer 7A from that time onwards, and stores the resonant frequency in the memory 30.

Also, in step S8, the control circuit 22 acquires or calculates a predetermined drive current value suitable for treatment, using the ID read from the read circuit 31 and stored in the memory 30.

The control circuit 22 acquires or calculates the predetermined drive current value using the LUT 32a or the parameters α and β according to, e.g., selection via the selection button 34c. Alternatively, the control circuit 22 determines the predetermined drive current value using both of the LUT 32a and the parameters α and β.

Also, in step S9, the control circuit 22 switches contacts in the switch circuit 23 to cause a current phase signal θi of the resonant frequency to be inputted to the reference-side input end R of the phase comparison circuit 24. Then, the power amplifier 27 is made to output a drive current in a PLL control loop state.

Furthermore, in step S10, with reference to a current detection value detected by the voltage and current detection circuit 28, the control circuit 22 controls the current amplification factor so that the value of the drive current for driving the ultrasound transducer 7A from the power amplifier 27 corresponds to the predetermined drive current value suitable for treatment, which has been acquired (calculated) in step S9.

Then, as indicated in step S11, the drive current outputted from the power amplifier 27 to the ultrasound transducer 7A is set to have the predetermined drive current value suitable for treatment. After the setting, as indicated in step S12, the surgeon performs treatment for therapy using the handpiece 3A.

Then, when the surgeon terminates the treatment, the surgeon operates, for example, an end button 34b provided in the operation section 34. As indicated in step S13, the control circuit 22 monitors an input of an ending operation. Upon an input of an ending operation, as indicated in step S14, the control circuit 22 stores historical information in association with the ID, in, for example, the historical information storage section 32d in the flash memory 32, and then powers off the power supply apparatus 4. Examples of the historical information includes, e.g., information on a date and a time of use of the handpiece 3J with the ID, information on the resonant frequency detected by the resonant frequency detection circuit 29 and information on a period of time of the output of the drive current from the power amplifier 27. Then, the processing indicated in FIG. 6 ends.

According to the present embodiment, even if ultrasound transducers 7J mounted in handpieces 3J to be detachably connected to the power supply apparatus 4 has variation in a characteristic of ultrasound vibration due to, e.g., the manufacturing process, a setting can be made to provide a predetermined drive current value suitable for treatment, which is set in advance according to the respective ultrasound transducer 7J, enabling treatment such as dissection or coagulation to be performed smoothly.

Figure 7:
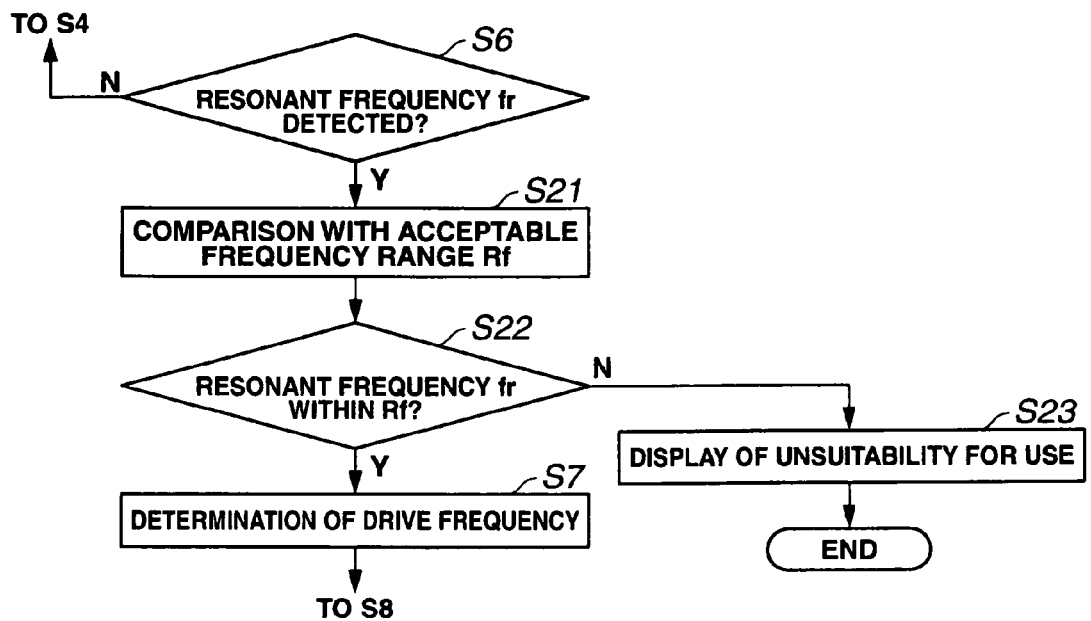
FIG. 7 is a flowchart illustrating processing for determining whether or not a resonant frequency falls within an acceptable frequency range.

Next, a content of processing where the determination section 22d is used will be described. In FIG. 7, whether or not the handpiece 3J connected to the power supply apparatus 4 is in a state suitable for use is determined by the determination section 22d determining whether or not the resonant frequency detected in step S6 of FIG. 6 falls within the frequency range indicated in FIG. 3.

An operation in this case is performed with, for example, processing in steps S21-S23 indicated in FIG. 7 added between steps S6 and S7 in FIG. 6.

In step S6, if a resonant frequency fr is detected, as indicated in step S21, the control circuit 22 compares the resonant frequency fr with a lower limit value and an upper limit value of an acceptable frequency range Rf in order to determine whether or not the resonant frequency fr falls within the acceptable frequency range Rf. Then, based on a result of the comparison, in next step S22, the control circuit 22 determines whether or not the detected resonant frequency fr falls within the acceptable frequency range Rf.

If the result of determination is that the detected resonant frequency fr falls within the acceptable frequency range Rf, the processing transitions to step S7. Processing step S7 onwards in FIG. 7 is similar to that in FIG. 6.

On the other hand, if it is determined that the resonant frequency fr detected in step S22 deviates from the acceptable frequency range Rf, as indicated in step S23, the control circuit 22 performs operation control to provide display of unsuitability for use. More specifically, the control circuit 22 outputs a message to the effect that the handpiece is a handpiece unsuitable for use to the display section 33, the display section 33 provides display of the unsuitability of use due to deviation of the resonant frequency fr from the acceptable frequency range Rf. Furthermore, display to urge replacement of the handpiece 3A to use a handpiece that can be used more properly may be provided. Then, the processing in FIG. 7 ends. In response to the display, the surgeon performs work for, e.g., replacement of the handpiece 3A in order to perform treatment more properly.

As result of the determination as above, the surgeon can perform treatment such as dissection or coagulation using a handpiece that ensures characteristics facilitating the treatment.

Figure 8A:
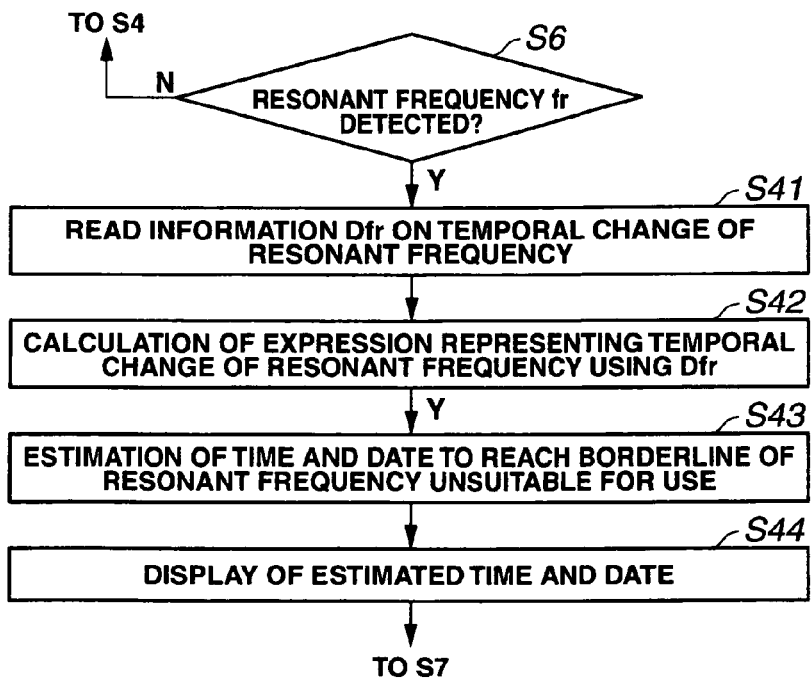
FIG. 8A is a flowchart illustrating a content of processing for estimating a period of time suitable for a treatment, using historical information.

FIG. 8A indicates processing for, when a repeatedly-used handpiece 3J is connected to the power supply apparatus 4, estimating (predicting) a date and a time to reach a borderline of the characteristics facilitating the treatment with reference to the historical information. In the processing, processing with reference to historical information is performed between, for example the processing in step S6 and the processing in step S7 in FIG. 6. The rest of the processing is similar to that in FIG. 6.

As indicated in FIG. 8A, in step S41 subsequent to the detection of the current resonant frequency fr in step S6, the control circuit 22 reads information on resonant frequency temporal change in past historical information for the handpiece 3J corresponding to the relevant ID.

Then, in next step S42, the control circuit 22 performs processing for calculating an approximate expression representing temporal resonant frequency change with proper reliability for near future, from past historical information and temporal resonant frequency data on the current resonant frequency fr.

Figure 8B:
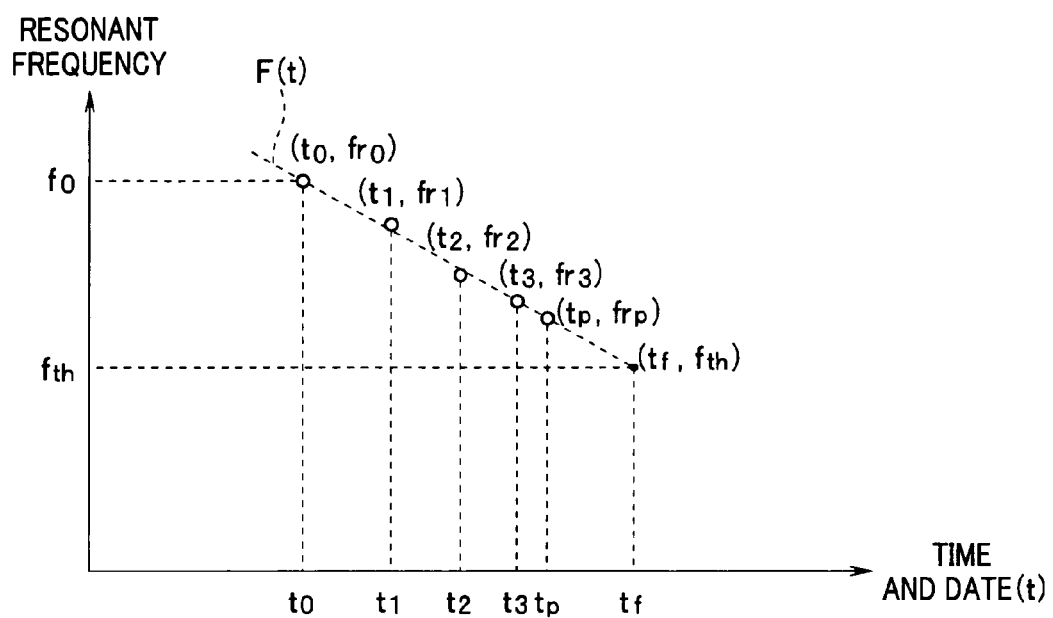
FIG. 8B is an illustrative diagram for calculating an approximate expression representing temporal change of a resonant frequency.

For example, as indicated in FIG. 8B, temporal changes in a resonant frequency frp up to current date and time tp relative to date and time to of first use and an initial resonant frequency fo on the date and time to are plotted on coordinates. In FIG. 8B, for example, resonant frequencies on dates and times t1, t2 and t3 are denoted by fr1, fr2 and fr3, respectively. The control circuit 22 calculates an approximate expression F(t) of a linear function representing resonant frequency temporal change using the data indicated in FIG. 8B.

In next step S43, the control circuit 22 estimates a date and a time (denoted as "tf") to reach a lower limit value fth of a resonant frequency, below which the handpiece 3J is unsuitable for use, using the approximate expression F(t). Then, in next step S44, the control circuit 22 performs processing for displaying the estimated date and time tf on the display section 33. After processing in step S44, the processing proceeds to step S7.

The surgeon considers, e.g., whether or not the used handpiece should be replaced, e.g., next time with reference to the estimated date and time tf. As described above, as a result of evaluation of an overview of a period of time in which a handpiece 3J can be used, a surgeon can more effectively use the handpiece.

Figure 9:
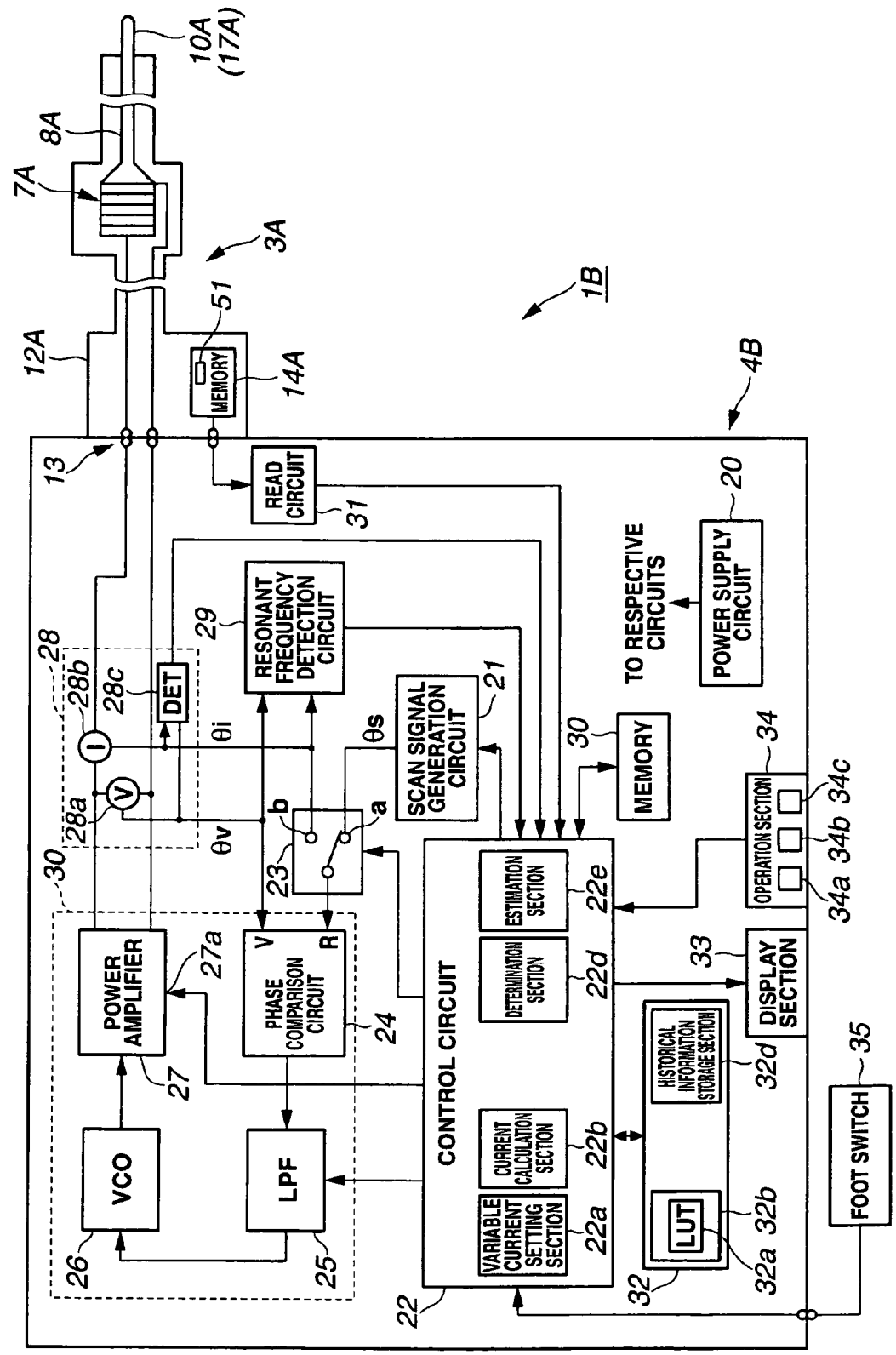
FIG. 9 is a diagram illustrating a configuration of an ultrasound surgery system according to a first modification of the first embodiment.

FIG. 9 illustrates a configuration of an ultrasound surgery system 1B according to a first modification. The ultrasound surgery system 1B includes a power supply apparatus 4B not including the parameter storage section 32c in the power supply apparatus 4 in the ultrasound surgery system 1 in FIG. 2. Also, in the ultrasound surgery system 1B, a handpiece 3J includes a parameter storage section 51 corresponding to the parameter storage section 32c inside the power supply apparatus 4.

In the above-described first embodiment, the parameter storage section 32c that stores IDs unique to respective handpieces 3J (to be detachably connected) together with parameters is provided on the power supply apparatus 4 side. In the present modification, as illustrated in FIG. 9, a parameter storage section 51 that stores parameters for calculating a predetermined drive current value for driving an ultrasound transducer 7J mounted in each handpiece to make ultrasound vibration at a predetermined value of amplitude or vibration velocity suitable for treatment is provided in a memory 14J (J=A in FIG. 9) on the respective handpiece 3J side. The rest of the configuration is similar to that of the first embodiment.

Note that FIG. 9 illustrates a more specific configuration of a voltage and current detection circuit 28. A drive signal outputted from two output ends of a power amplifier 27 is applied to opposite electrodes of the ultrasound transducer 7J, whereby the ultrasound transducer 7J makes ultrasound vibration.

The voltage and current detection circuit 28 includes a voltage detection circuit 28a (abbreviated as "V" in FIG. 9) that detects a voltage of the drive signal outputted from the two output ends of the power amplifier 27, and a current detection circuit 28b (abbreviated as "I" in FIG. 9) that detects a current (drive current) flowing in the ultrasound transducer 7J. The voltage detection circuit 28a outputs a signal of the detected voltage as a voltage phase signal θv, and the current detection circuit 28b outputs a signal of the detected current as a current phase signal θi. Also, each of the voltage phase signal θv and the current phase signal θi is detected by a detector circuit 28c using, e.g., a diode, and an effective value or a peak value of each of the detected voltage and the detected current is outputted to the control circuit 22, as a voltage value or a current value.

Figure 10:
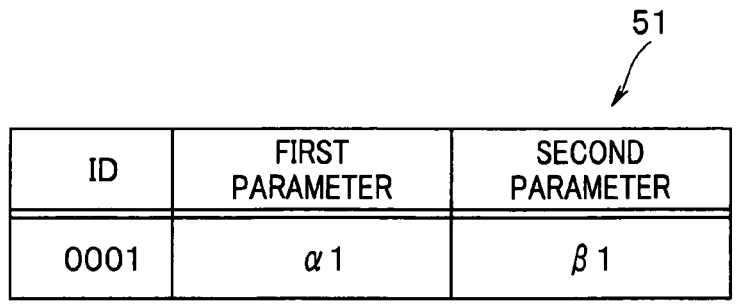
FIG. 10 is a diagram illustrating contents of parameters stored in a parameter storage section provided inside a connector in the first modification.

FIG. 10 illustrates an example of parameters stored in the parameter storage section 51. In the present modification, a read circuit 31 reads parameters α and β together with an ID from the memory 14J and outputs the parameters α and β and the ID to the control circuit 22. The control circuit 22 stores the ID and the parameters α and β in, e.g., a memory 30. In this state, basically, the configuration of the present modification is substantially similar to that of the first embodiment, and accordingly, the present modification provides operations and effects that are similar to those of the first embodiment. Note that in the case of the present modification, historical information stored in the flash memory 32 may be stored in the memory 14J.

In this case, the read circuit 31 is changed to a read/write circuit that can perform writing in the memory 14J.

For the configuration in FIG. 2 or 9, a case where information for determining or calculating a predetermined drive current value is stored in both of the respective handpiece 3J side and the power supply apparatus 4 side has been described.

Figure 11:
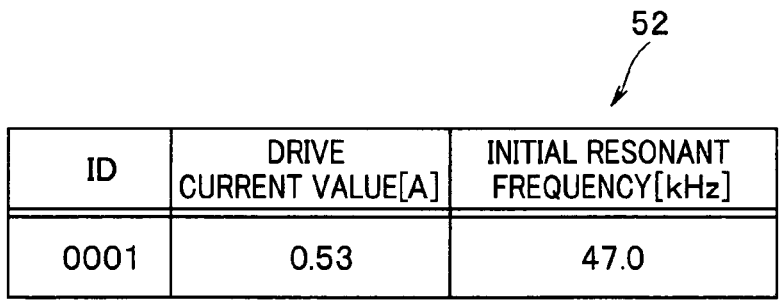
FIG. 11 is a diagram illustrating a drive current value being stored in a current value storage section provided inside a connector in a second modification.

On the other hand, as illustrated in FIG. 11, a current value storage section 52 that stores a predetermined drive current value for making an ultrasound transducer 7J mounted in each handpiece 3J have ultrasound vibration at a predetermined value of amplitude or vibration velocity suitable for treatment may be provided in a memory 14J in the handpiece 3J. Then, a control circuit 22 acquires the predetermined drive current value from the current value storage section 52 via a read circuit 31, and a variable current setting section 22a in the control circuit 22 may perform control so that a drive current outputted by a power amplifier 27 becomes the predetermined drive current value. Note that as illustrated in FIG. 11, an initial resonant frequency may be stored in the memory 14J.

Figure 12:
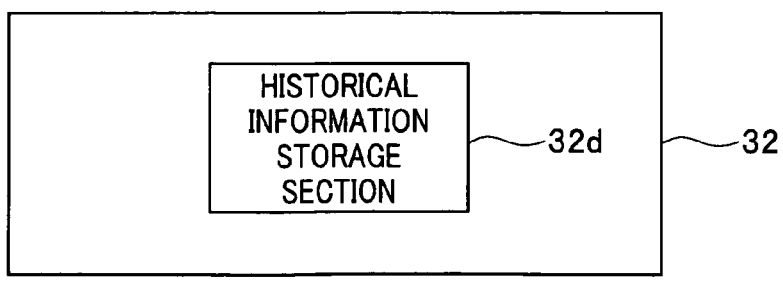
FIG. 12 is a diagram illustrating information stored in a flash memory provided inside a power supply apparatus in the second modification.

As described above, if a predetermined drive current value is stored in each handpiece 3J, a power supply apparatus having a configuration not including the LUT storage section 32b in the power supply apparatus 4B in FIG. 9 can be employed. In other words, as illustrated in FIG. 12, a flash memory 32 only needs to have a configuration provided with a historical information storage section 32d alone that stores historical information. Also, a configuration in which no historical information is stored may be employed.

In the above-described embodiment and modifications, a configuration in which one of a plurality of handpieces 3J can selectively be connected to, e.g., the power supply apparatus 4 or 4B has been described. On the other hand, in the case of an ultrasound surgery system having a configuration in which only one handpiece (denoted by 3K) is connected to one power supply apparatus (denoted by 4D), the power supply apparatus 4D may be configured to store or calculate a predetermined drive current value for making an ultrasound transducer (denoted by 7K) in the handpiece 3K have ultrasound vibration at a predetermined value of amplitude or vibration velocity suitable for treatment, without the need to identify the handpiece.

Note that embodiments formed by, e.g., partially combination of the above-described embodiment and the like also belong to the present invention. For example, where a predetermined drive current value for ultrasound vibration at a predetermined value of amplitude or vibration velocity suitable for treatment varies as a resonant frequency detected by a resonant frequency detection circuit varies, a notice urging handpiece replacement may be provided if the drive current value varies by, for example, around no less than 15 percent relative to a standard drive current value (for example, 0.53 A). Also, the ultrasound transducer 7J provided in each handpiece 3J is not limited to one including a langevin transducer formed by bolt fastening.

What is claimed is:

1. An ultrasound surgery system comprising:
a handpiece including an ultrasound transducer capable of generating ultrasound vibration and a probe joined to the ultrasound transducer, the probe being capable of transmitting the ultrasound vibration generated by the ultrasound transducer to a treatment portion;
a power supply apparatus for driving the ultrasound transducer, the power supply apparatus allowing the handpiece to be detachably connected thereto;
a drive current output section provided in the power supply apparatus, the drive current output section being configured to produce a drive current for driving the ultrasound transducer mounted in the handpiece connected to the power supply apparatus and output the produced drive current to the ultrasound transducer;
a drive frequency output section provided in the power supply apparatus, the drive frequency output section being configured to detect a drive frequency for driving the ultrasound transducer mounted in the handpiece connected to the power supply apparatus, with a resonant frequency of the ultrasound transducer, and output the detected drive frequency;
a first information storage section configured to store first information including a parameter based on identification information unique to the handpiece connected to the power supply apparatus, the first information being referred to when, in order to keep an amplitude or a vibration velocity of the ultrasound vibration in the treatment portion of the handpiece at a predetermined value according to the handpiece, a predetermined drive current value to be outputted to the ultrasound transducer, the predetermined drive current value corresponding to the predetermined value, is determined;
a current calculation section configured to calculate the predetermined drive current value to be outputted to the ultrasound transducer; and
a variable current setting section provided in the power supply apparatus, the variable current setting section being configured to variably set the drive current so that the drive current produced by the drive current output section, based on both (i) the parameter stored in the first information storage section and (ii) the drive frequency detected by the drive frequency output section, has the predetermined drive current value, in order to keep the amplitude or the vibration velocity of the ultrasound vibration in the treatment portion provided at a distal end portion of the probe in the handpiece connected to the power supply apparatus at the predetermined value.

2. The ultrasound surgery system according to claim 1, wherein the first information storage section is provided inside the handpiece.

3. The ultrasound surgery system according to claim 1, wherein the first information storage section is provided inside the power supply apparatus.

4. The ultrasound surgery system according to claim 3, wherein the first information storage section includes information on the predetermined drive current value as the first information.

5. The ultrasound surgery system according to claim 3,
wherein the handpiece further stores identification information unique to the handpiece; and
the first information storage section includes a look-up table storage section configured to store the predetermined drive current value associated with each of a plurality of pieces of unique identification information in a form of a look-up table.

6. The ultrasound surgery system according to claim 1, wherein the current calculation section includes a linear function current calculation section configured to calculate the predetermined drive current value using a linear function in which the drive frequency detected by the drive frequency output section is a variable and the parameter is included.

7. The ultrasound surgery system according to claim 1, wherein the first information storage section is provided inside the power supply apparatus, and the first information storage section stores a plurality of pieces of the first information set so as to respectively conform to a plurality of the handpieces to be selectively connected to the power supply apparatus.

8. The ultrasound surgery system according to claim 1, wherein the first information storage section is provided inside each of the handpieces to be detachably connected to the power supply apparatus.

9. The ultrasound surgery system according to claim 1, wherein the current calculation section includes a first current calculation section configured to calculate the predetermined drive current value based on a first characteristic in which the drive frequency detected by the drive frequency output section is a variable and as the drive frequency is larger, the predetermined drive current value becomes larger.

10. The ultrasound surgery system according to claim 1, wherein the current calculation section includes a second current calculation section configured to calculate the predetermined drive current value based on a second characteristic in which the drive frequency detected by the drive frequency output section is a variable and as the drive frequency is larger, the predetermined drive current value becomes smaller.

11. The ultrasound surgery system according to claim 1, further comprising a current storage section configured to store the predetermined drive current value associated with the parameter.

12. The ultrasound surgery system according to claim 1, further comprising:
a frequency information storage section configured to store, in advance, information on a resonant frequency at which the ultrasound transducer mounted in the handpiece detachably connected to the power supply apparatus resonates and an acceptable frequency range based on the resonant frequency; and
a determination section configured to determine whether or not the resonant frequency actually detected by the drive frequency output section, at which the ultrasound transducer resonates, falls within the frequency range.

13. The ultrasound surgery system according to claim 1, further comprising:
a historical information storage section configured to store historical information including a resonant frequency for the handpiece connected to the power supply apparatus and used for processing; and
an estimation section configured to estimate a date and a time for the resonant frequency to reach a borderline of a predetermined frequency range, from information in temporal change of the resonant frequency in the historical information.

14. The ultrasound surgery system according to claim 1, wherein the drive current output section provides a phase-locked loop circuit that performs phase control for the ultrasound transducer connected to the power supply apparatus so as to make the drive frequency follow the resonant frequency in order to maintain the resonant frequency for the ultrasound transducer as the drive frequency.

15. The ultrasound surgery system according to claim 1, wherein the ultrasound transducer includes a langevin transducer including a plurality of piezoelectric elements fastened together.

* * * * *